(12) United States Patent
West et al.

(10) Patent No.: US 6,171,072 B1
(45) Date of Patent: Jan. 9, 2001

(54) COMBINATION ASPIRATOR PUMP AND AIR COMPRESSOR APPARATUS FOR USE IN MEDICAL PROCEDURES

(75) Inventors: Joe E. West; Reginald H. Fowler, both of Meridian, TX (US)

(73) Assignee: Scion Valley, Inc., Meridian, TX (US)

( * ) Notice: Under 35 U.S.C. 154(b), the term of this patent shall be extended for 0 days.

(21) Appl. No.: 09/285,551

(22) Filed: Apr. 2, 1999

(51) Int. Cl.$^7$ ........................................... F04B 49/00
(52) U.S. Cl. ............................. 417/298; 417/290
(58) Field of Search .................. 137/340; 165/47; 417/137, 298, 290, 313; 62/64; 159/25.2; 604/317, 35; 606/127; 433/104, 77

(56) References Cited

U.S. PATENT DOCUMENTS

| | | | |
|---|---|---|---|
| 3,374,122 | * 3/1968 | Cousins | 137/340 |
| 4,243,040 | * 1/1981 | Beecher | 606/127 |
| 4,359,085 | * 11/1982 | Mueller | 165/47 |
| 4,857,063 | * 8/1989 | Glenn | 604/317 |
| 4,902,226 | * 2/1990 | Elliott et al. | 433/104 |
| 5,007,803 | * 4/1991 | DiVito et al. | 417/137 |
| 5,177,975 | * 1/1993 | Mertens | 62/64 |
| 5,211,558 | * 5/1993 | Bailey et al. | 433/77 |
| 5,222,871 | * 6/1993 | Meyer et al. | 417/313 |
| 5,352,194 | * 10/1994 | Greco et al. | 604/35 |
| 5,551,845 | * 9/1996 | Milam | 417/290 |
| 5,741,397 | * 4/1998 | Kraver | 159/25.2 |

* cited by examiner

Primary Examiner—Teresa Walberg
Assistant Examiner—Leonid Fastovsky
(74) Attorney, Agent, or Firm—Akin, Gump, Strauss, Hauer & Feld, LLP (57) ABSTRACT

A combination electric motor driven vacuum pump and air compressor unit, particularly adapted to use in medical procedures, is mounted in an insulated cabinet arranged to provide for drawing cooling air into the cabinet through an inlet duct, cause cooling air to flow over an aftercooler part of a compressed air discharge conduit to aftercool compressed air, and cause cooling air to flow through the pump/compressor unit and be discharged from the cabinet. A pressure air receiver tank is mounted in the cabinet and is operably connected to a condensate receiver and a control valve for discharging condensate to an evaporator container connected to the aftercooler conduit part to evaporate condensate. A control circuit includes solenoid actuated valves for controlling vacuum produced by the pump/compressor unit and actuation of a flexible tube clamp mechanism for cutting off vacuum from a vacuum device, such as a cannula, during certain phases of a liposuction medical procedure, for example. A manual vacuum release valve is also connected to the pump/compressor unit for manually releasing vacuum to allow replacement or emptying of a debris collection canister disposed between the flexible tube clamp and the pump/compressor unit suction port. Vacuum pressure may be selectively controlled by controls including a vacuum sensor, a potentiometer controller and a comparator circuit.

23 Claims, 6 Drawing Sheets

COMBINATION ASPIRATOR PUMP AND AIR COMPRESSOR APPARATUS FOR USE IN MEDICAL PROCEDURES

FIELD OF THE INVENTION

The present invention pertains to an electric motor driven, compact, combination vacuum pump and air compressor apparatus, particularly adapted for use in medical procedures.

BACKGROUND OF THE INVENTION

Certain medical procedures require a source of controlled vacuum or aspiration as well as a source of compressed air. For example, liposuction procedures require a controllable source of vacuum for aspirating debris that is removed during the liposuction procedure through an aspirating cannula and the like. In this regard, it has been considered desirable to provide such a vacuum source as a compact, quiet, electric motor driven pump apparatus which is easily controllable to control the vacuum pressure and airflow. Since a vacuum pump may also be operated as an air compressor it is desirable to provide this feature in an electric motor driven apparatus which is otherwise adapted primarily for use as a vacuum source.

Generally, a combination vacuum pump and air compressor unit adapted for use in medical procedures should be light weight, quiet and portable. For example, it would be desirable to mount the apparatus on a stanchion or the like in the vicinity of the medical procedure itself so that the user of the source of vacuum may adjust the operating parameters of the apparatus.

As a consequence of the need for a compact, quiet and easily controlled motor driven combination vacuum pump and air compressor apparatus, certain requirements of such an apparatus have posed problems in the development thereof. These problems have been solved by the present invention as will be appreciated by those skilled in the art.

SUMMARY OF THE INVENTION

The present invention provides a compact motor driven vacuum pump or aspirator and air compressor apparatus, particularly useful in medical procedures.

In accordance with one aspect of the present invention a combination aspirator or vacuum pump and air compressor apparatus is provided which includes a control system operable to automatically convert operation of the apparatus between a vacuum pump and an air compressor and provide simultaneous operation by operation of remotely and automatically controlled valves. Vacuum control and pressure air control are carried out by automatic regulators. The apparatus includes a control system which is operable to provide rapid shutoff of vacuum, which is advantageous for a certain medical procedures, such as liposuction procedures.

In accordance with another aspect of the invention an electric motor driven vacuum pump/compressor apparatus is provided with a control system which reduces a start-up load on the pump motor.

In accordance with still another aspect of the invention an advantageous arrangement for pump discharge air aftercooling or heat exchange is provided and a compressed air reservoir or receiver tank is provided with controls to automatically drain condensate to a condensate evaporator container which is arranged to exchange heat with the pump/compressor unit aftercooler.

Still further in accordance with the invention, a compact, electric motor driven, combination vacuum pump and air compressor unit is provided with a cabinet which includes a unique cooling air flow circuit, improved sound suppression and may be easily mounted on a stanchion or floor or table mounted, if desired.

The above described features of the invention together with other important aspects thereof will be further appreciated by those skilled in the art upon reading the detailed description which follows in conjunction with the drawing.

DETAILED DESCRIPTION OF A PREFERRED EMBODIMENT

In the description which follows like parts are marked throughout the specification and drawing with the same reference numerals, respectively. The drawing figures are not necessarily to scale and certain elements may be shown exaggerated in scale or in somewhat schematic or generalized form in the interest of clarity and conciseness.

Figure 1:
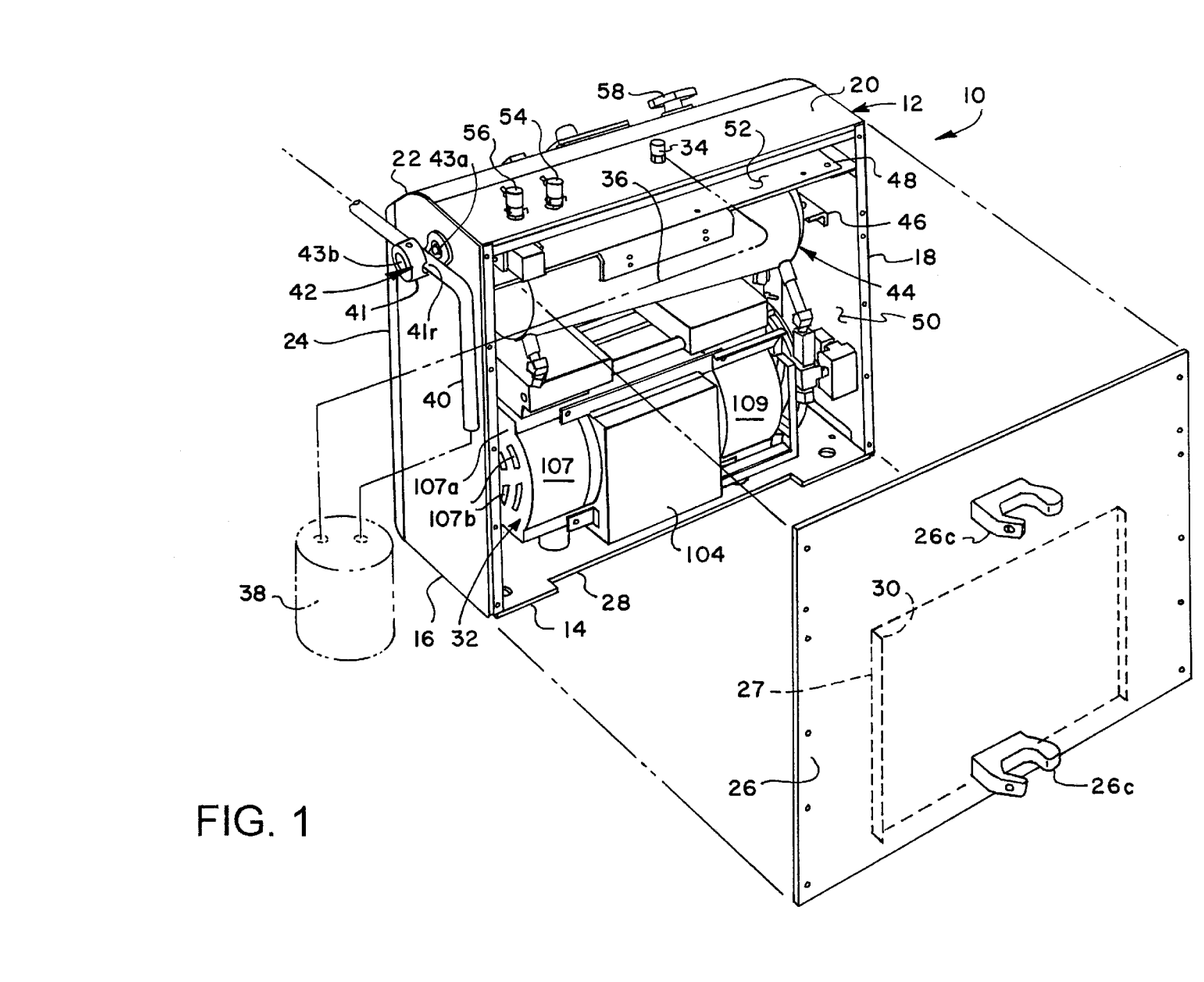
FIG. 1 is a perspective view of a compact, electric motor driven combination vacuum pump or aspirator and air compressor apparatus in accordance with the invention.

Referring to FIG. 1, a combination vacuum pump and air compressor apparatus in accordance with the invention is illustrated and generally designated by the numeral 10. The apparatus 10 includes an enclosure or cabinet 12 comprising a bottom wall 14 opposed endwalls 16 and 18, a top wall 20 including a slopping panel portion 22, a front wall 24 and a removable rear wall 26. The cabinet 12 may be formed of sheet metal, for example, and suitable panels of sound suppression material, not shown in FIG. 1, may be applied to the inside surfaces of one or more of the cabinet walls to minimize noise transmission from the apparatus 10. A cooling air inlet duct 27 is secured to the inside surface of the rear wall 26, opens to a port 28 in the bottom wall 14 and is provided with a discharge port 30 for admitting cooling air to the interior of the cabinet 12. Rear wall 26 includes two spaced apart apparatus support clamps 26c mounted thereon for advantageously supporting a tubular stanchion, not shown, for supporting other medical apparatus used in conjunction with the apparatus 10.

An electric motor driven vacuum pump/compressor unit 32 is mounted in the interior of the cabinet 12 on the bottom wall 28 by a suitable mounting arrangement to be described in further detail herein. The pump/compressor unit 32 may be generally of a type commercially available, such as a 71R Series manufactured by Gast Manufacturing, Inc. of Benton Harbor, Mich. The vacuum pump/compressor unit 32 includes a suitable suction or inlet port, not shown in FIG. 1, which is connected to a suction conduit, including a fitting 34. In a preferred arrangement of the apparatus 10, operating as a vacuum pump, a flexible conduit 36 is connected to the fitting 34 and to a debris collection tank or canister 38. The canister 38 is also connected to a flexible conduit 40 which extends transversely through a generally tubular fitting 41 suitably mounted on endwall 16 and comprising part of a pressure air operated clamp mechanism 42 for forcibly clamping the conduit 40 to substantially close off all flow of fluid therethrough. Tubular fitting 41 includes a transverse slot or recess 41r formed therein for releasably receiving a portion of conduit 40, as shown. Typically, the conduit 40 is connected to a medical instrument, such as a cannula, not shown in FIG. 1, used in liposuction procedures and it is desirable to provide instant shutoff of fluid flow into and through the cannula and the conduit 40 to the canister 38 under certain operating conditions in the procedure.

As further shown in FIG. 1, the apparatus 10 includes a pressure air receiver or reservoir tank 44 mounted within the cabinet 12 on suitable spaced apart brackets 46, one shown, secured to the opposed endwalls 16 and 18, respectively. The compressed air receiver 44 is mounted within the cabinet 12 below a transverse intermediate wall 48 which separates an interior space 50 within the cabinet 12 from a space 52 in which electrical control components are preferably located. The top wall 20 supports respective fittings 54 and 56 which are connected to suitable conduits, not shown in FIG. 1, connected to the pressure air receiver 44 and to an exhaust air conduit, also not shown, which may be connected to a suitable device using pressure air from the receiver 44. Suitable operating controls and display means are mounted on the front depending panel wall portion 22 which will be described in further detail herein, including an operating handle 58 for a vacuum control valve.

Figure 2:
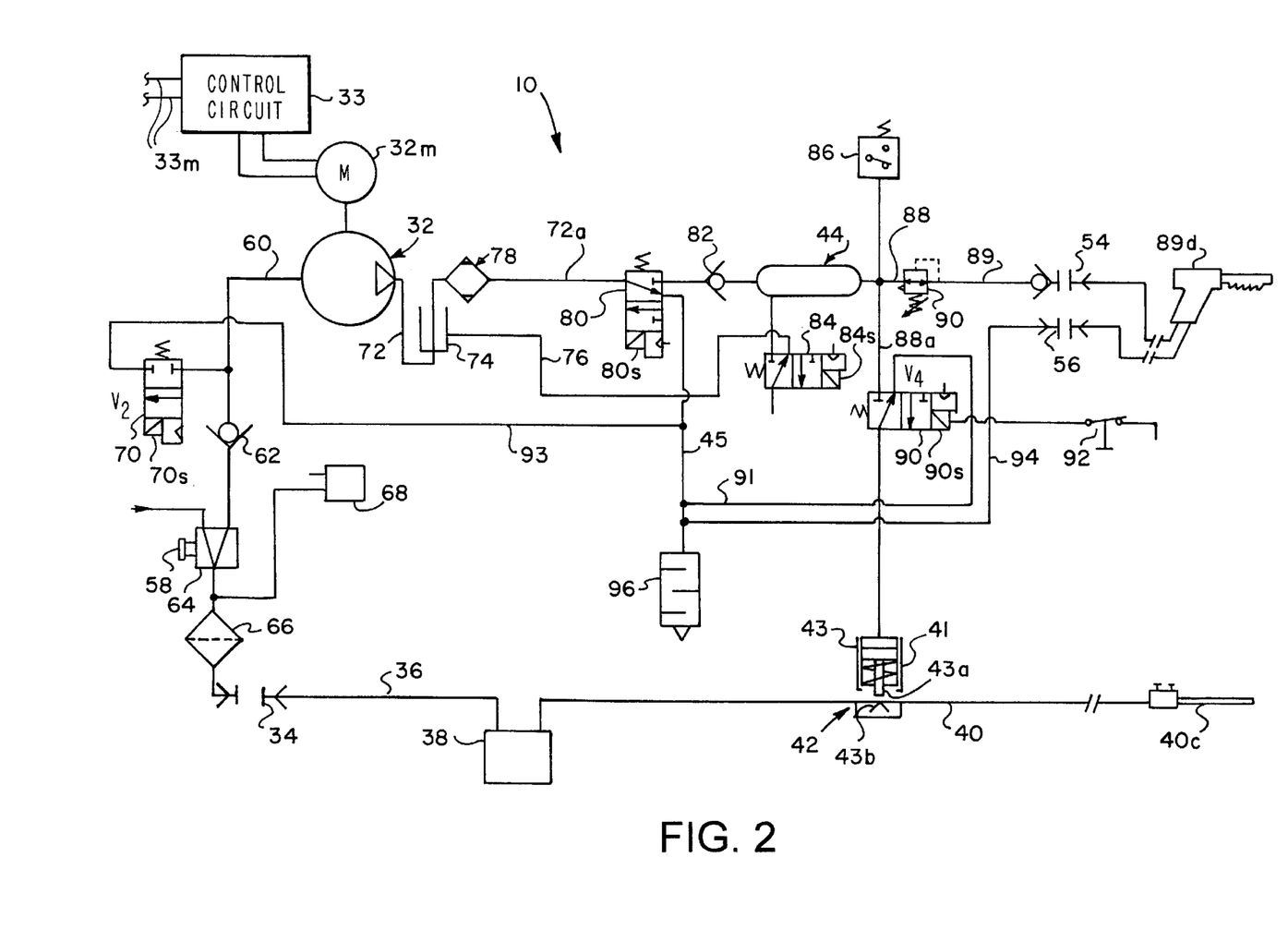
FIG. 2 is a schematic diagram of major components of the apparatus shown in FIG. 1.

Referring now to FIG. 2, there is illustrated a schematic diagram of the basic components of the apparatus 10 including control valves for handling fluid flow to and from the vacuum pump/air compressor unit 32. As shown in FIG. 2, the pump/compressor unit 32 includes a suitable electric drive motor 32m and is connected to an inlet conduit 60, which includes a conventional check valve 62 interposed therein, a vacuum control valve 64 and an inlet air filter 66 connected to the fitting 34. A suitable vacuum sensor 68 detects the amount of vacuum or absolute pressure in conduit 60 at the point indicated in the circuit. The sensor 68 may be of a type commercially available such as a model 5100 DPX available from Motorola, Inc. The vacuum control valve 64 is a manually actuated valve which may be operated while the pump/compressor unit 32 is running to interrupt suction or vacuum on the conduit 36 and the canister 38 to permit changing canisters during operation of the apparatus 10 without shutting off the pump/compressor unit 32. Actuation of the valve 64 will connect the suction or inlet conduit 60 to atmosphere to allow the pump/compressor unit 32 to continue running and providing compressed air, if needed, while removing any vacuum pressure from the conduit 36 and canister 38. A solenoid actuated valve 70 is operably interposed in conduit 60 and is adapted to be controlled to provide a predetermined vacuum in conduit 36, 40 as will be explained in further detail herein.

The pump/compressor unit 32 is connected to a discharge conduit 72 which extends through an open top condensate evaporator container 74 which is connected to a condensate discharge conduit 76. Conduit 72 is also connected to a heat exchanger or aftercooler coil 78 for cooling pressure air discharged from the pump/compressor unit 32. A solenoid actuated valve 80 is interposed in conduit 72 upstream of a check valve 82 and pressure air receiver 44. Condensate accumulating in pressure air receiver 44 is operable to be discharged into a condensate receiver 45 by way of a solenoid actuated valve 84. Valve 84 is also connected to conduit 76 for discharging condensate from the receiver 45 to the condensate evaporator container 74 which evaporates condensate rapidly when pump/compressor unit 32 is discharging hot, compressed air to the receiver 44. A pressure switch 86 is operably connected to a pressure air discharge conduit 88 which is operable to receive pressure air from the receiver or reservoir 44. A conventional pressure regulator 90 is also interposed in conduit 88. Valve 80 is operable to supply pressure air from pump/compressor unit 32 to receiver 44 or bypass pressure air from unit 32 to a silencer or muffler 96 for return to atmosphere.

As further shown in FIG. 2, the vacuum conduit clamp mechanism 42 is operably connected to pressure air conduit 88 by way of a branch conduit 88a having a solenoid actuated valve 90 interposed therein. Valve 90 is controlled by a manually actuatable switch 92, which is preferably a foot operated switch. The operator of the apparatus 10 may actuate switch 92 to effect imposing pressure air on tube clamp mechanism 42, which includes a spring return pressure fluid cylinder and piston type actuator 43. Actuator 43 includes a piston rod 43a which is pressure air biased to pinch the flexible conduit 40 against a suitable anvil 43b to provide rapid, controlled cutoff of vacuum in conduit 40 between a device, such as a cannula 40c, connected to the conduit and the canister 38.

A pressure air operated device 89d may be suitably connected to the apparatus 10 by way of pressure air supply conduit 89 and connector 54. An exhaust or return air conduit 94 may also be connected to such device by way of connector 56 for returning spent pressure air to muffler 96 disposed within the cabinet or enclosure 12. Muffler 96 is also operably connected to clamp mechanism 42 by way of valve 90 and a conduit 91. Muffler 96 is also connected to the pump/compressor unit inlet conduit 60 by way of solenoid actuated valve 70 and a connecting conduit 93. Air is flowable in both directions through muffler 96.

Figure 3:
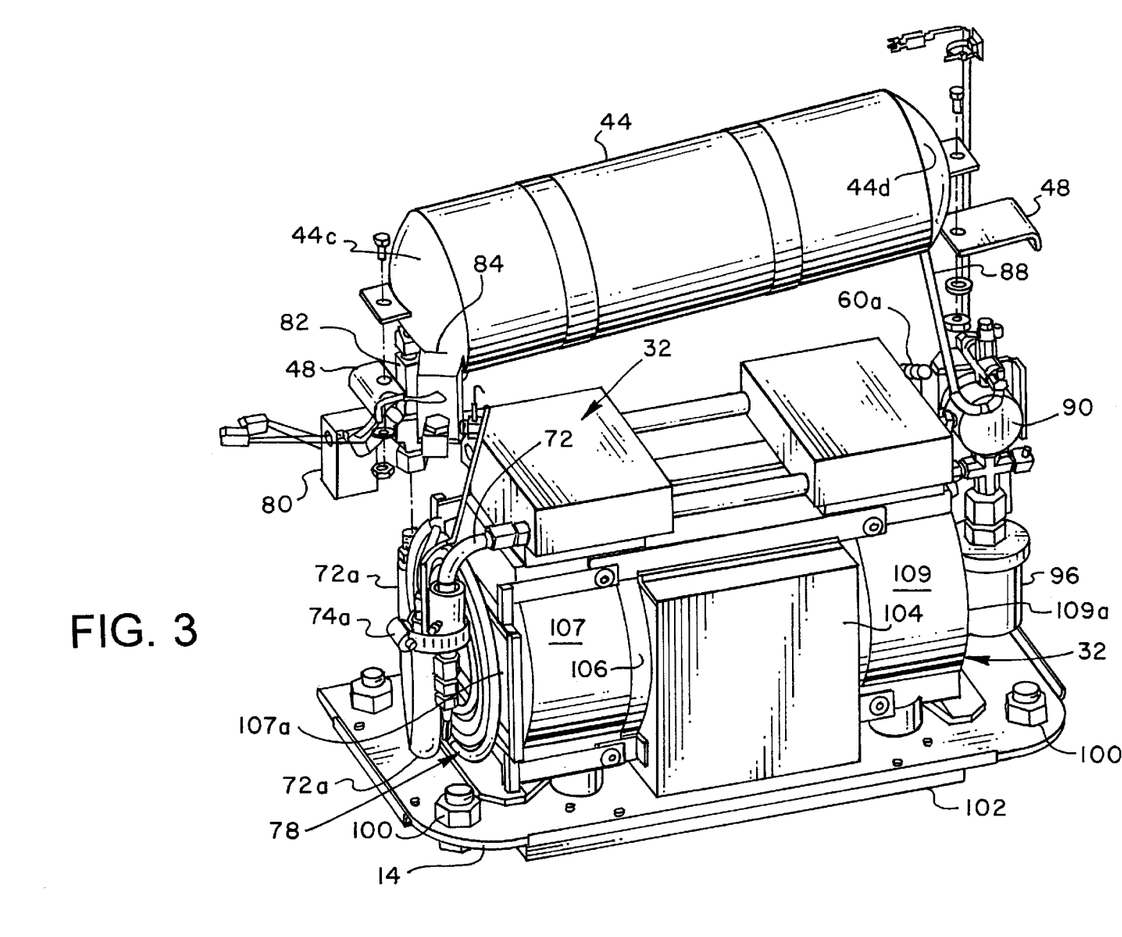
FIG. 3 is an exploded perspective view of the motor driven pump/compressor unit, the compressed air receiver tank and related mounting or support members.

Referring now to FIG. 3, further features of the apparatus 10 are illustrated showing the pump/compressor unit 32 mounted on the bottom wall 14 of the cabinet 12 with the remainder of the cabinet removed. As shown in FIG. 3 the bottom wall 14 is provided with four spaced apart feet, three shown, comprising hollow hex-head bolt and nut assemblies 100 which are adapted to support suitable caster assemblies, not shown, or similar support members operable to permit standoff of the bottom wall 14 from a surface on which the apparatus 10 may be supported. The standoff position of the bottom wall 14 is also provided to allow clearance for a cooling air discharge duct 102 secured to the bottom side of wall 14 and to be described in further detail herein.

Figure 4:
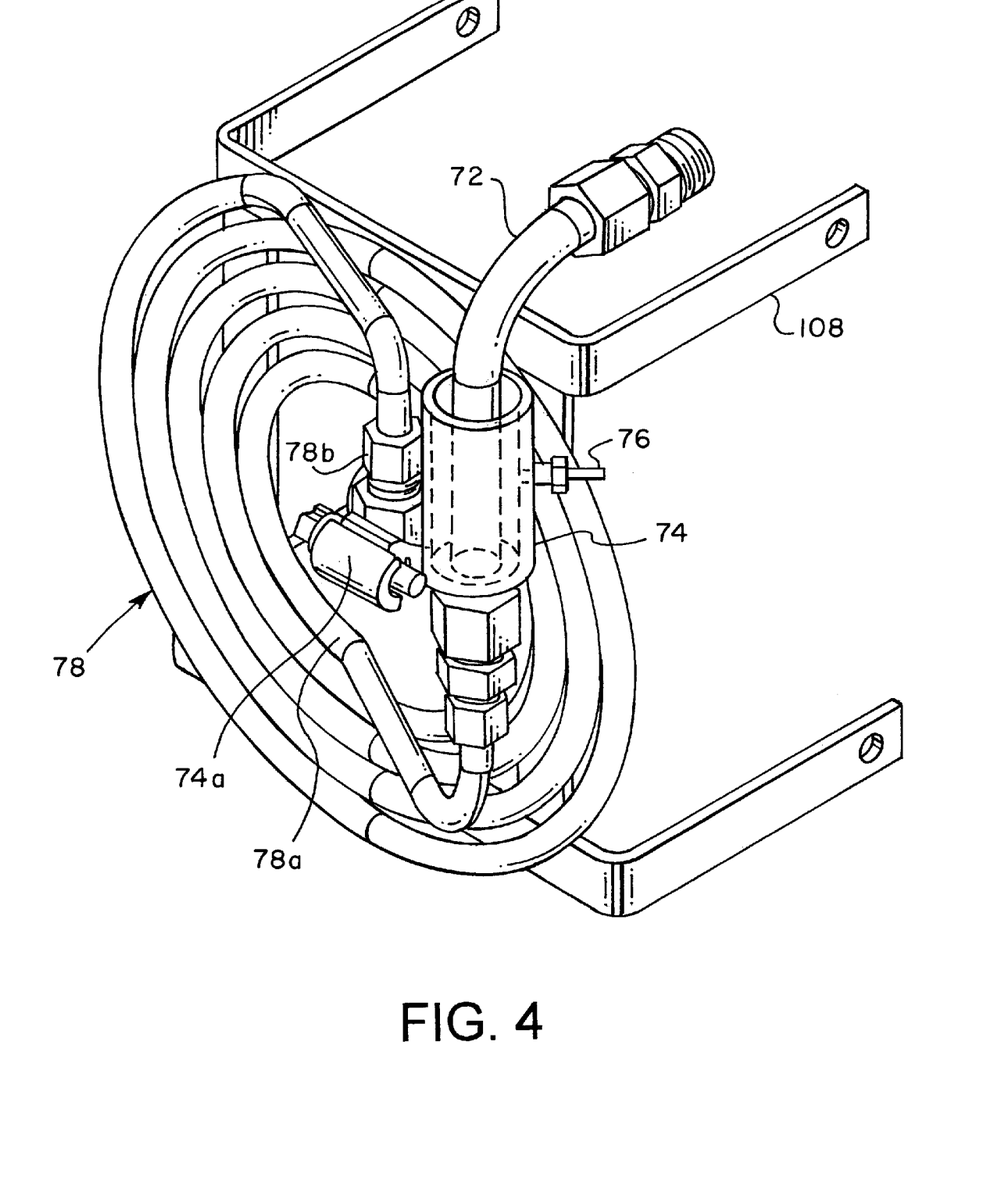
FIG. 4 is a detail perspective view of the pump discharge air aftercooler coil and condensate evaporator container.

The pump/compressor unit 32 includes an inlet fitting 60a adapted to be connected to conduit 60, not shown in FIG. 3. The pump/compressor unit 32 is also provided with opposed cooling air discharge shrouds or ducts 104, one shown in FIG. 3, mounted on a motor housing member 106 for the unit drive motor 32m. Cooling air is drawn into the pump/compressor unit 32 through opposed pump housings 107, 109, at respective end walls 107a and 109a, by suitable motor driven fans, not shown in FIG. 3, and such cooling air is then discharged into the shrouds 104 and through a suitable opening, also not shown in FIG. 3, in bottom wall 14 and into the duct 102 for discharge to atmosphere. Pressure air is discharged from the pump/compressor unit 32 at discharge manifold 32a into conduit 72, which extends through the condensate evaporator container 74, see FIG. 4 also, and pressure air circulates through the heat exchanger or aftercooler 78, which is preferably characterized as a coiled metal tube 78a, as shown in FIG. 4. A suitable fitting 78b is connected to the discharge end of the coiled heat exchange tube 78a for connecting the heat exchanger or aftercooler 78 to discharge conduit 72a, FIGS. 2 and 3. The fitting 78b is suitably secured to the evaporator container 74 by a conventional band clamp 74a.

As shown in FIG. 4, the heat exchanger or aftercooler 78 is mounted on a suitable bracket 108 for mounting on the pump/compressor unit 32 so that the coiled conduit or tube 78a is disposed across the pump housing end face or end wall 107a in proximity thereto and whereby cooling air may flow over the conduit 78a and through ports 107b, FIG. 1, to cool pressure air flowing therethrough. Bracket 108 is detachably mountable on the pump/compressor unit 32, as shown in FIG. 3. FIG. 3 also illustrates both support brackets 48 for supporting the pressure air receiver 44 on the opposed end walls 16 and 18 of the cabinet 12. Solenoid valves 80 and 84 are mounted to a suitable fitting which includes the check valve 82, FIG. 3, adjacent an end 44c of receiver 44, which is canted downward with respect to the opposite end 44d, so that condensate accumulating within the receiver 44 will flow toward the end 44c for discharge therefrom to condensate receiver 45, not shown in FIG. 3. FIG. 3 also illustrates the general arrangement of receiver discharge conduit 88, pressure regulator 90 and muffler 96. Accordingly, the components of the apparatus 10 are compactly arranged within the space 50 provided by the cabinet 12.

Figure 5:
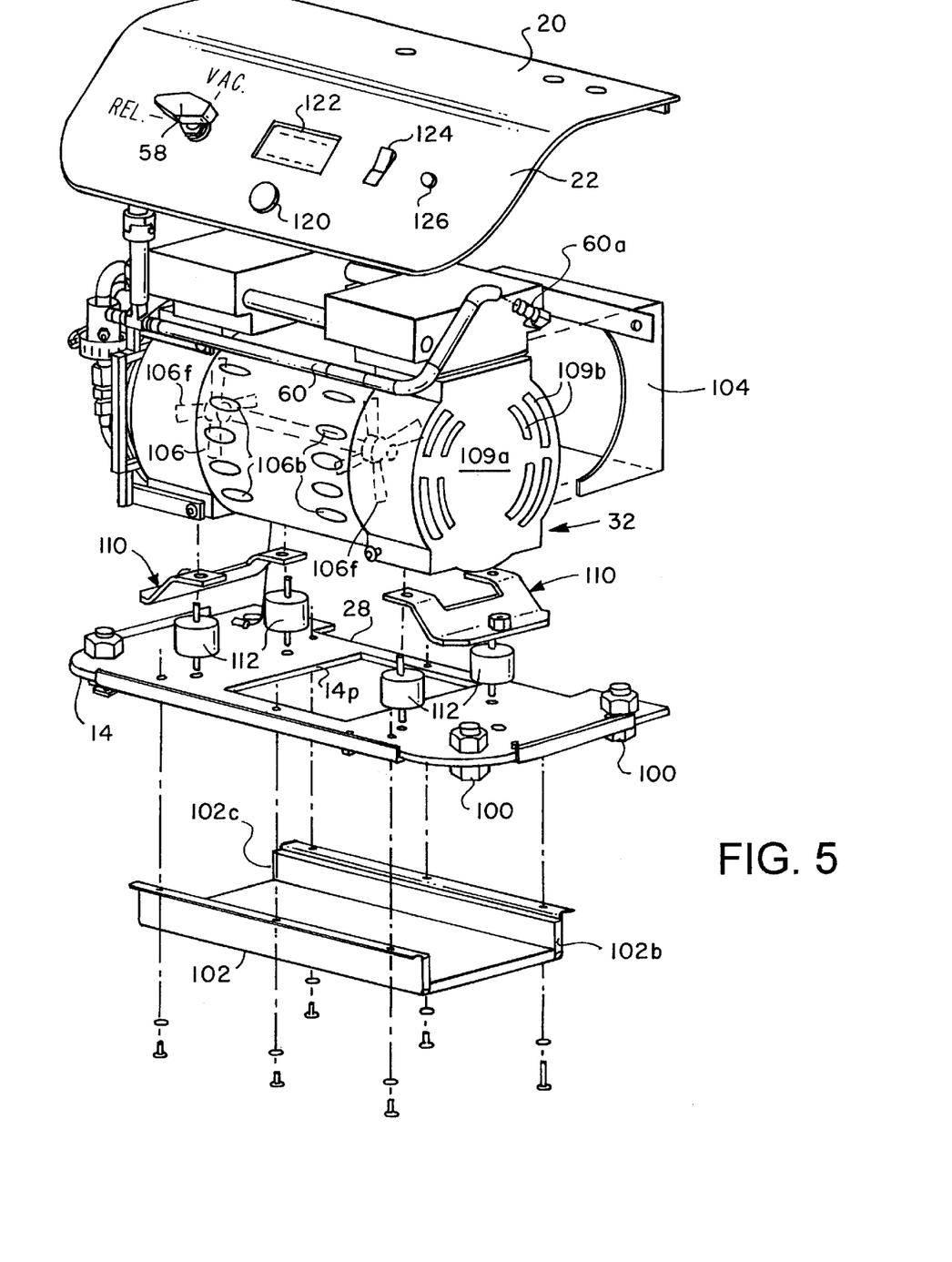
FIG. 5 is an exploded perspective view showing certain other components of the pump/compressor unit, its support structure and cooling air ducting.

Referring now to FIG. 5, there is illustrated further details of the apparatus 10 including certain components mounted on the bottom wall 14. The pump/compressor unit 32 is suitably mounted on spaced apart mounting brackets 110 which are vibration and sound isolated from the bottom wall 14 by suitable elastomeric isolators 112, as illustrated. FIG. 5 also illustrates the cooling air discharge duct 102 which is adapted to be removably mounted on the bottom side of the bottom wall 14. FIG. 5 further illustrates a cooling air discharge port 14p formed in the bottom wall 14 for discharging cooling air from the shrouds or ducts 104, one shown in FIG. 5, into the duct 102. As shown in FIG. 5, the pump/compressor unit 32 is also provided with suitable cooling air inlet openings or ports 109b in housing end wall 109a and cooling air discharge openings 106b are formed in motor housing 106. Accordingly, cooling air is drawn into the housings 107 and 109 through the end walls 107a and 109a and discharged through openings 106b to flow downward as directed by the shrouds 104 through the port 14p and through the channel-shaped cooling air discharge duct 102 to atmosphere at opposite ends 102b and 102c. FIG. 5 also illustrates portions of the suction conduit 60 arranged along the front side of the pump/compressor unit 32.

The general arrangement of the apparatus 10 is believed to be understandable to those of ordinary skill in the art from the foregoing description. By providing the cabinet 12 with the cooling air inlet duct 27 arranged as illustrated and described, ambient air may be drawn into the duct 27 and discharged into the spaces 50 and 52 for circulation over the electrical control elements which are mounted generally in the space 52 on the transverse wall 48. Cooling air also flows over the air receiver 44 and within the space 50 and then generally into the pump/compressor unit 32 through the ports 107b and 109b as induced by motor driven cooling air fans 106f, FIG. 5. Cooling air is discharged through the openings or ports 106b and into the shrouds 104, directed downwardly through the port 14p and discharged from the cabinet 12 toward the opposed end walls 16 and 18 through the duct 102. In this way heated cooling air which is being discharged from the apparatus 10 does not tend to mix with ambient cooling air entering the apparatus through the port 28 and the cooling air duct 27. Substantially the entire interior surfaces of the cabinet walls 16, 18, 20, 24 and 26 may be lined with a suitable acoustic insulation material. Still further, an insulation blanket, not shown, may be draped over the pump/compressor unit 32 adjacent the rear wall 26 before fastening the rear wall to the cabinet 12, using conventional fasteners, not shown.

Referring again briefly to FIG. 5, the top wall 20 and display panel part 22 are shown with certain components mounted on the panel part including the operating handle 58 for the vacuum release valve 64, a rotary control knob 120 for the vacuum adjustment control, a digital visual display 122 for displaying the vacuum pressure setting, a main power off/on switch 124 and a visual indicator 126 which indicates the operating condition of the tube clamp actuator mechanism 42.

In a typical operating procedure for the system 10, prior to energizing the motor 32m of the pump/compressor unit 32, the actuator handle 58 is turned to the position to provide that the valve 64 will allow producing a vacuum in conduit 36 and canister 38 when the unit 32 is energized. The actual vacuum produced in conduit 36 may be adjusted by adjusting the position of control knob 120 which will effect control over the operation of pump/compressor unit 32 in a manner to be described hereinbelow. Upon energization of the apparatus 10 by actuation of switch 124 pump/compressor unit 32 will begin producing a vacuum which may be adjusted by adjusting the position of the knob 120 and reading the vacuum selected on display 122. Switch 92, which is a normally closed switch, is open when actuated by the operator's foot to release the clamp actuator mechanism 42 to allow vacuum to be pulled on the conduit 40 through the canister 38. However, prior to inserting a vacuum device, such as a cannula, not shown, into a patient's body during a medical procedure the switch 92 is actuated to energize valve 90 to cause the actuator mechanism 42 to clamp flexible conduit 40 thereby shutting off any vacuum being pulled through the aforementioned device. However, a vacuum will still exist in canister 38 and throughout the conduit system connected to the inlet of the pump/compressor unit 32. This condition will exist, of course, until actuator handle 58 is turned to cause valve 64 to release vacuum in conduit 36 and canister 38. Thus, vacuum is released in canister or container 38, at will, to allow the container to be emptied of any collected debris or replaced by another container without shutting down the apparatus 10.

Accordingly, a preselected vacuum condition may be obtained within conduit 40 connected to the aforementioned vacuum device, and the canister 38, which vacuum condition may be selectively varied by a control circuit to be described herein. Moreover, the referenced control circuit is also operable to minimize the load on the pump/compressor unit motor 32m on startup. During operation of the apparatus 10, if it is desired to change the container or canister 38, it is preferable to energize the actuator mechanism 42 to clamp the flexible conduit 40 cutting off vacuum from being pulled on the aforementioned vacuum device and also operate valve 64 to release vacuum in conduit 36 and container 38 so that the container or canister may be emptied or replaced. Accordingly, it is not necessary to deenergize motor 32m to change the container or canister 38.

Figure 6:
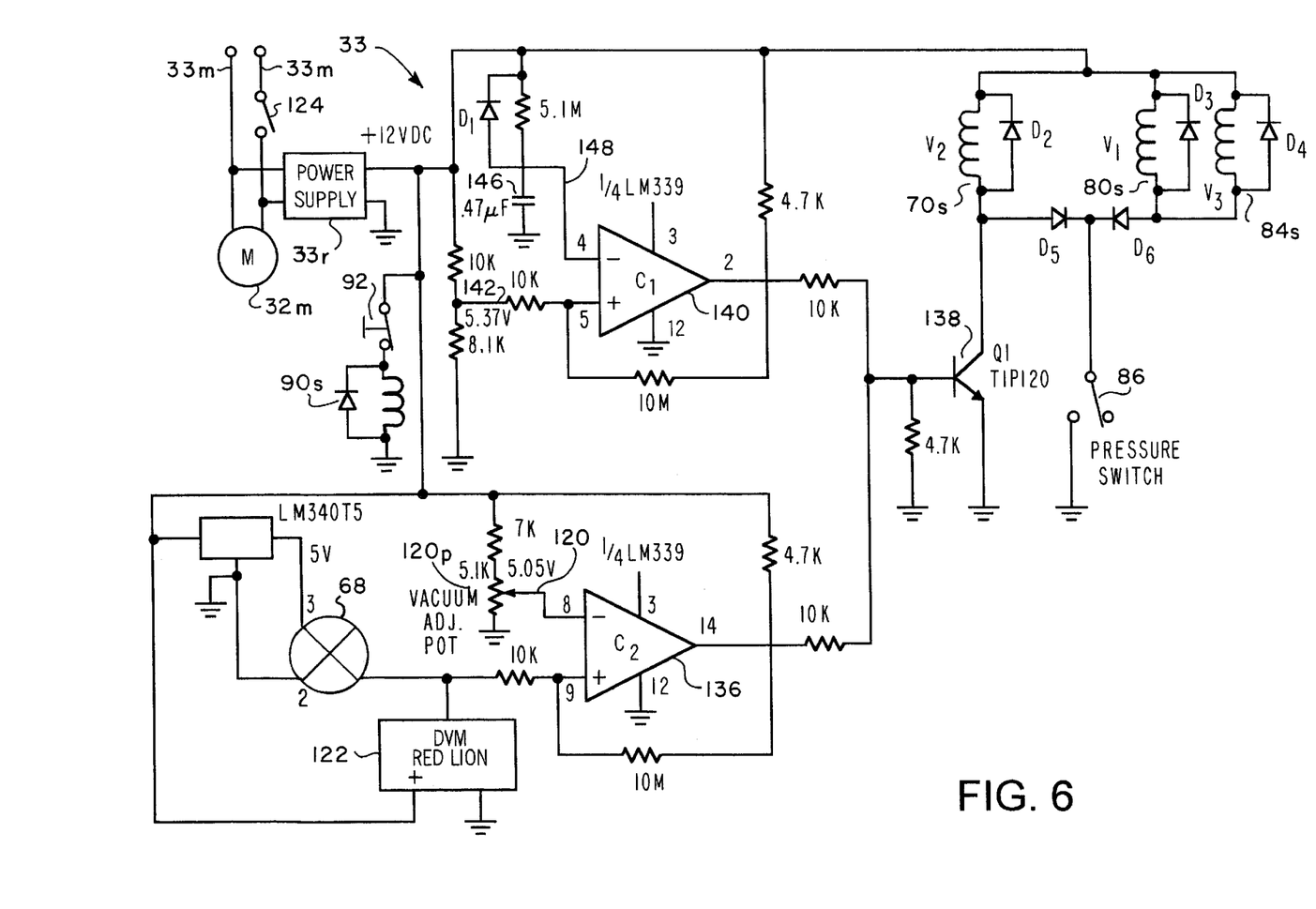
FIG. 6 is a schematic diagram showing electrical control circuitry for the combination vacuum pump and air compressor apparatus of the present invention.

Referring now briefly to FIG. 6, there is illustrated a portion of the control circuit 33 for the apparatus 10 including that portion which receives one hundred ten volt AC power for operating motor 32*m* through mains 33*m*. Twelve volt DC power is supplied via a regulated power supply 33*r* to the vacuum sensor 68 and the digital display 122. As shown in FIG. 6, the vacuum adjustment control knob 120 is operably connected to a potentiometer 120*p* which, together with a conductor from sensor 68, is connected to a comparator 136. Accordingly, an output voltage signal from the sensor 68 is input into comparator 136 together with an input voltage signal from the potentiometer 120*p*. As input voltage from the potentiometer 120*p* is increased above that of the output signal from the sensor 68 an output signal from comparator 136 goes low, turning off current flow through a transistor 138. Under these conditions, solenoid 70*s* for valve 70 is deenergized and valve 70 closes so that the pump/compressor unit 32 now pulls vacuum through check valve 62, valve 64, filter 66, conduit 36 and canister 38. If actuator mechanism 42 is deenergized, vacuum is pulled through conduit 40 and any vacuum device connected thereto. Suitable means, not shown, provides operating voltage to comparators 136 and 140.

When the preset vacuum pressure level is reached and the output signal from the sensor 68 reaches that of the voltage reference signal from the potentiometer 120*p*, comparator 136 turns on or goes high and causes valve 70 to be energized opening valve 70 to atmosphere to pull ambient air through muffler 96. Accordingly valve 70 cycles between open and closed positions to maintain a predetermined vacuum condition in the apparatus 10, including the conduit 36, canister or container 38 and conduit 40.

In order to reduce the electrical load on the motor 32*m* at start up conditions the portion of the control circuit 33 illustrated in FIG. 6 includes comparator 140 which receives a signal at motor startup from conductor 142 which produces an output signal from comparator 140 to cause current to flow through transistor 138 energizing valve 70 to move to the open position to minimize any vacuum load on the pump/compressor unit 32. Capacitor 146 charges over an interval of about 1.50 seconds, at which time current flows through conductor 148 to comparator 140 causing comparator 140 to turn off or go low thereby interrupting current through transistor 138 and causing valve 70 to close to allow vacuum to be pulled by the pump/compressor unit 32 through conduits 36 and 40, depending on the position of valve 64.

At initial startup, the receiver/reservoir 44 is unpressurized and the pressure switch 86 is in a closed position to energize the solenoid actuators 70*s*, 80*s* and 84*s*. Energizing solenoid 70*s* causes valve 70 to move to the open position to pull air through muffler 96 and conduit 93. Solenoid 80*s*, when energized, causes valve 80 to move to a position to conduct pressure air from pump/compressor unit 32 to receiver 44 and valve 84, when energized by its solenoid 84*s*, will move to a position to dump condensate from receiver 44 to condensate receiver 45.

If conduit 89 is blocked, such as not having a connector part connected to the conduit at connector 54, or if any apparatus connected to the conduit 89 which will consume pressure air pressure is not operating, switch 86 will open at a preset air pressure of about 60 psig to 80 psig, for example. When such preset pressure is reached in receiver tank 44 solenoid actuators 70*s*, 80*s* and 84*s* are deenergized and valve 84 is moved to a position to discharge condensate collected in receiver 45 into the container 74. During operation of the pump/compressor unit 32, the heated conduit 72 will cause such condensate to evaporate. Valve 80 will also be moved to the deenergized position to provide for conducting air discharged from the pump/compressor unit 32 to atmosphere through muffler 96. Valve 70 will also be moved to the position to begin pulling a vacuum through conduit 60, check valve 62 and valve 64, and such vacuum will be subject to control by the other features of the control system and apparatus described hereinbefore.

Accordingly, the operation of the apparatus 10, together with the important features and advantages described herein before, is believed to be readily apparent to those skilled in the art, from the foregoing description. Those components not described in detail or identified by a commercial source may be fabricated by conventional engineering materials used for vacuum pump/compressor apparatus and may be obtained or devised by the routineer in the art of vacuum pump/compressor units used for medical procedures.

Although a preferred embodiment of the invention has been described in detail herein those skilled in the art will recognize that various substitutions and modifications may be made to the apparatus 10 without departing from the scope and spirit of the appended claims.

What is claimed is:

1. A combination vacuum pump and air compressor apparatus, particularly adapted for use in medical procedures, said apparatus comprising:

a motor driven vacuum pump/air compressor unit including an inlet conduit and a discharge conduit, a part of said inlet conduit being connected to a vacuum operated device;

a compressed air receiver tank adapted to be connected to said discharge conduit for receiving pressure air from said pump/compressor unit;

a first control valve operably connected to said inlet conduit for controlling vacuum pressure in said inlet conduit; and control means for operating said first control valve to selectively provide vacuum pressure in said inlet conduit and to release the vacuum pressure in said part of said inlet conduit.

2. The apparatus set forth in claim 1 including:

a second control valve operably connected to said inlet conduit, and said control means includes means for causing one of said control valves to move to an open position to minimize vacuum pressure in said inlet conduit during startup of said motor.

3. The apparatus set forth in claim 2 wherein:

said first control valve includes an actuator for effecting release of vacuum pressure in said part of said inlet conduit, at will.

4. The apparatus set forth in claim 2 wherein:

said control means includes a control circuit including a potentiometer, a comparator for receiving a selected voltage signal from said potentiometer, a vacuum sensor for sensing vacuum pressure in said inlet conduit and operable to produce a voltage signal to said comparator, said comparator being operable to produce an output signal for effecting operation of said one control valve to maintain a predetermined vacuum pressure in said inlet conduit.

5. The apparatus set forth in claim 1 wherein:

said pump/compressor unit is mounted in a cabinet forming an enclosure for said apparatus, said pump/compressor unit includes a motor driven cooling air fan operable to induce cooling air flow through said pump/compressor unit when said motor is energized, said cabinet includes a cooling air inlet duct for admitting cooling air to an interior space and at least one cooling air discharge shroud operably connected to said pump/compressor unit for discharging heated cooling air from said cabinet, the flow of cooling air into and out of said cabinet being induced by said cooling air fan.

6. The apparatus set forth in claim 5 wherein:
said cabinet includes a bottom wall and a rear wall and said cooling air inlet duct is formed on said rear wall and includes an inlet port in said bottom wall for admitting cooling air to said cabinet.

7. The apparatus set forth in claim 5 wherein:
said bottom wall includes a cooling air discharge duct in communication with said cooling air discharge shroud connected to said pump/compressor unit for receiving heating cooling air therefrom.

8. The apparatus set forth in claim 1 wherein:
said pump/compressor unit includes a compressed air aftercooler part of said discharge conduit mounted adjacent one end of said pump/compressor unit, said one end including cooling air inlet port means therein for drawing motor cooling air over said part of said discharge conduit to effect cooling of compressed air discharged from said pump/compressor unit.

9. The apparatus set forth in claim 1 including:
a control valve connected to said discharge conduit between said pump/compressor unit and said receiver tank and operable to be moved to a position to bypass discharged air from said pump/compressor unit when air pressure in said receiver tank has reached a predetermined maximum pressure.

10. In a vacuum pump apparatus particularly adapted for use in medical procedures, a motor driven vacuum pump unit including an inlet conduit and a discharge conduit, at least a first control valve operably connected to said inlet conduit for controlling vacuum pressure in said inlet conduit, control means for operating said first control valve to selectively control vacuum pressure in said inlet conduit, a flexible conduit operably connected to said inlet conduit, and a clamp mechanism operably connected to said flexible conduit to effect shutoff of vacuum pressure in said flexible conduit.

11. The apparatus set forth in claim 10 wherein:
said flexible conduit and said inlet conduit are operably connected to a canister for receiving debris flowing through said flexible conduit from a vacuum device connected to said flexible conduit.

12. The apparatus set forth in claim 10 including:
a compressed air receiver connected to said discharge conduit for receiving pressure air from said pump unit and a valve interconnecting said clamp mechanism with said compressed air receiver for energizing said clamp mechanism at will.

13. The apparatus set forth in claim 10 including:
a second control valve operably connected to said inlet conduit, and said control means includes means for causing one of said control valves to move to an open position to minimize vacuum pressure in said inlet conduit during startup of said motor.

14. The apparatus set forth in claim 10 wherein:
said first control valve includes an actuator for effecting release of vacuum pressure in said inlet conduit, at will.

15. A combination vacuum pump and air compressor apparatus, particularly adapted for use in medical procedures, said apparatus comprising:
a motor driven vacuum pump/air compressor unit including an inlet conduit and a discharge conduit;
a compressed air receiver tank adapted to be connected to said discharge conduit for receiving pressure air from said pump/compressor unit;
a first control valve operably connected to said inlet conduit for controlling vacuum pressure in said inlet conduit;
a flexible conduit operably connected to said inlet conduit and to a vacuum operated device; and
a clamp mechanism operably connected to said flexible conduit to effect shutoff of vacuum pressure in said flexible conduit and said device.

16. A combination vacuum pump and air compressor apparatus, particularly adapted for use in medical procedures, said apparatus comprising:
a motor driven vacuum pump/air compressor unit including an inlet conduit and a discharge conduit:
a compressed air receiver tank adapted to be connected to said discharge conduit for receiving pressure air from said pump/compressor unit;
an aftercooler including part of said discharge conduit for cooling pressure air being discharged from said pump/compressor unit; and
a condensate evaporator container operably associated with said part of said discharge conduit and operable to receive condensate from said compressed air receiver to effect evaporation of said condensate by heat transferred from said part of said discharge conduit.

17. A combination vacuum pump and air compressor apparatus, particularly adapted for use in medical procedures, said apparatus comprising:
a motor driven vacuum pump/air compressor unit including an inlet conduit and a discharge conduit;
said pump/compressor unit being mounted in a cabinet forming an enclosure for said apparatus, said pump/compressor unit including a cooling air fan drivenly connected to said motor and operable to induce cooling air flow into said cabinet and over at least part of said pump/compressor unit when said motor is energized;
said cabinet includes a cooling air inlet duct for admitting cooling air to an interior space in said cabinet and at least one cooling air discharge shroud operably connected to said pump/compressor unit for receiving cooling air to flow over said at least part of said pump/compressor unit and discharging heated cooling air from said cabinet, the flow of cooling air into and out of said cabinet being induced by said cooling air fan; and
a compressed air aftercooler part of said discharge conduit mounted adjacent said pump/compressor unit and within said cabinet, said part of said discharge conduit being disposed such that said cooling air fan is operable for drawing motor cooling air over said part of said discharge conduit to effect cooling of compressed air discharged from said pump/compressor unit.

18. The apparatus set forth in claim 17 including:
a compressed air receiver tank disposed in said cabinet and adapted to be connected to said discharge conduit for receiving pressure air from said pump/compressor unit.

19. The apparatus set forth in claim 15 wherein:
said flexible conduit and said inlet conduit are operably connected to a canister for receiving debris flowing through said flexible conduit from said device.

20. The apparatus set forth in claim 15 wherein:
said apparatus includes a valve interconnecting said clamp mechanism with said compressed air receiver and operable to be actuated for energizing said clamp mechanism at will.

21. The apparatus set forth in claim 17 wherein:

said cabinet includes a bottom wall and a rear wall and said cooling air inlet duct is formed on said rear wall and includes an inlet port in said bottom wall for admitting cooling air to said cabinet.

22. The apparatus set forth in claim 17 wherein:

said bottom wall includes a cooling air discharge duct in communication with said cooling air discharge shroud connected to said pump/compressor unit for receiving heating cooling air therefrom.

23. A combination vacuum pump and air compressor apparatus, particularly adapted for use in medical procedures, said apparatus comprising:

a motor driven vacuum pump/air compressor unit including an inlet conduit and a discharge conduit;

said pump/compressor unit being mounted in a cabinet forming an enclosure for said apparatus, said pump/compressor unit including a cooling air fan operable to induce cooling air flow into an interior space within said cabinet and over at least part of said pump/compressor unit when said motor is energized;

said cabinet includes a bottom wall and a rear wall and a cooling air inlet duct formed on said rear wall for conducting cooling air to said interior space;

an inlet port in said bottom wall for admitting cooling air to said inlet duct;

at least one cooling air discharge shroud operably connected to said pump/compressor unit for discharging heated cooling air from said cabinet, the flow of cooling air into and out of said cabinet being induced by said cooling air fan; and said bottom wall includes a cooling air discharge duct in communication with said cooling air discharge shroud for receiving heated cooling air therefrom.

\* \* \* \* \*